(12) United States Patent
Elliott

(10) Patent No.: US 8,637,566 B2
(45) Date of Patent: Jan. 28, 2014

(54) SLOW INFUSION OF SULCARDINE AND ITS SALTS

(75) Inventor: Gary T. Elliott, Portland, ME (US)

(73) Assignee: HUYA Bioscience International LLC, San Diego, CA (US)

( * ) Notice: Subject to any disclaimer, the term of this patent is extended or adjusted under 35 U.S.C. 154(b) by 68 days.

(21) Appl. No.: 13/509,739

(22) PCT Filed: Nov. 16, 2010

(86) PCT No.: PCT/US2010/056849
§ 371 (c)(1),
(2), (4) Date: May 14, 2012

(87) PCT Pub. No.: WO2011/062903
PCT Pub. Date: May 26, 2011

(65) Prior Publication Data
US 2012/0245214 A1     Sep. 27, 2012

Related U.S. Application Data

(60) Provisional application No. 61/261,927, filed on Nov. 17, 2009.

(51) Int. Cl.
*A61K 31/4025*     (2006.01)

(52) U.S. Cl.
USPC .......................................................... 514/422

(58) Field of Classification Search
USPC .......................................................... 514/422
See application file for complete search history.

(56) References Cited

U.S. PATENT DOCUMENTS

2012/0245214 A1*    9/2012   Elliott ........................... 514/422
2012/0309810 A1*   12/2012   Elliott ........................... 514/422

* cited by examiner

*Primary Examiner* — Raymond Henley, III
(74) *Attorney, Agent, or Firm* — Foley & Lardner LLP

(57) ABSTRACT

A composition comprised of an active agent that is 4-methoxy-N-(3,5-bis-(1-pyrrolidinyl)-4-hydroxy benzyl)benzene sulfonamide or a pharmaceutically acceptable salt thereof is intravenously administered to a subject, substantially evenly over a period of greater than about 15 minutes, to avoid disadvantageous hemodynamic effects, including systemic diastolic and systolic hypotension, to can occur with rapid intravenous or even short-term infusion administration of the active agent.

18 Claims, 1 Drawing Sheet

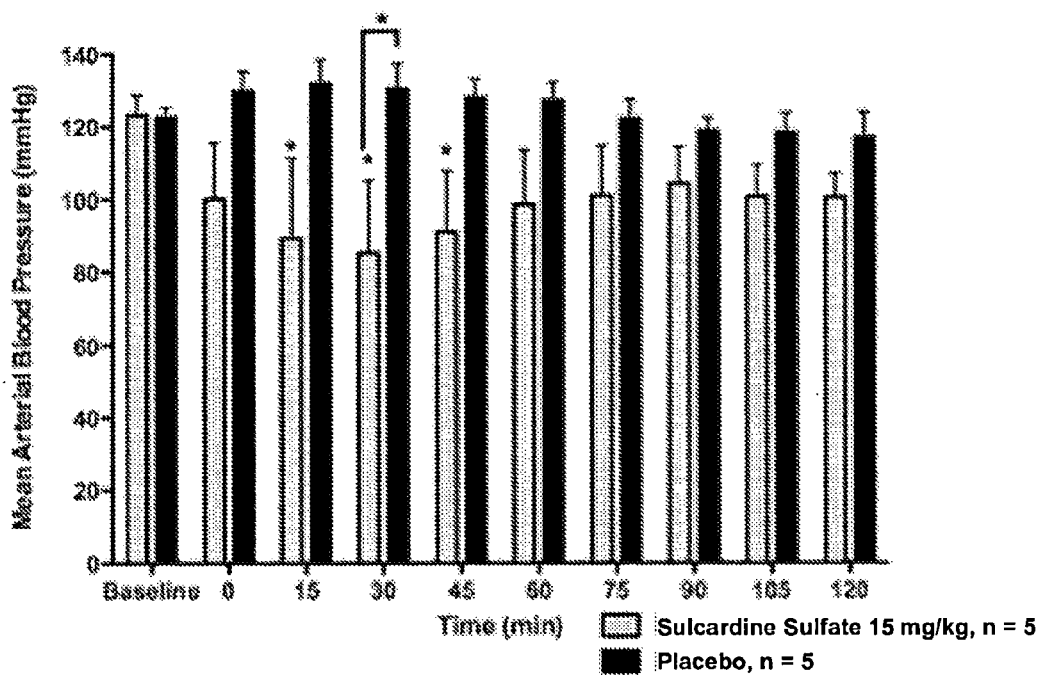

SLOW INFUSION OF SULCARDINE AND ITS SALTS

CROSS-REFERENCE TO RELATED PATENT APPLICATIONS

This application claims priority to U.S. Provisional Application No. 61/261,927, filed Nov. 17, 2009, the entire contents of which are incorporated herein by reference.

FIELD OF INVENTION

This invention relates methodology for administering 4-methoxy-N-(3,5-bis-(1-pyrrolidinyl)-4-hydroxy benzyl) benzene sulfonamide (sulcardine) and pharmaceutically acceptable salts of sulcardine, in the context of treating cardiac arrhythmia.

BACKGROUND OF THE INVENTION

Throughout this disclosure, various publications, patents and published patent specifications are referenced by an identifying citation. The disclosures of these publications, patents and published patent specifications are hereby incorporated by reference in their entirety into the present disclosure, thereby to describe the state of the art to which this invention pertains.

Cardiac arrhythmia, also known as "dysrhythmia," is a rubric for a group of conditions characterized by abnormal electrical activity in the heart. Examples of arrhythmias include premature ventricular contractions, ventricular tachycardia, ventricular fibrillation and supraventricular tachyarrhythmia such as atrial fibrillation. By example, atrial fibrillation (AF) is a supraventricular tachyarrhythmia characterized by uncoordinated atrial activation with consequent deterioration of atrial mechanical function. Persistent and/or chronic AF is associated with increased risk of thromboembolic events including MI and stroke and heart failure. Theories of the mechanism of AF involve two main processes: enhanced automaticity in one or several rapidly depolarizing foci and reentry involving one or more circuits.

AF is the most common arrhythmia requiring medical care, with a prevalence of almost 1% in the adult U.S. population (projection of 6 million in U.S. in 2006 and 9 million by 2020). Its prevalence increases with age, such that 8% of people >80 years old have AF. As U.S. and European demographics shift toward an older population, AF will become an even more prevalent cardiovascular disease. Recurrent episodes of AF occur in patients on average 50%/year. Accordingly, AF is a major strain on the health care system, with an average cost in the United States of $3600 per case per annum.

AF is associated with symptoms which adversely affect quality of life including, for example, shortness of breath, chest discomfort or pain and exercise intolerance. The longer the patient remains in AF the greater the risk of thrombus formation in the atria and hence risk of thromboembolic stroke, and hence the need for chronic anticoagulant therapy. It is felt that a large percentage of all stroke cases in the U.S. are secondary to persistent or chronic AF. Other serious cardiac events occurring at significantly higher incidence in AF patients include heart failure and myocardial infarction (MI).

Treatment of AF revolves around cardioversion and use of anticoagulents in persistent and chronic cases. Cardioversion of patients with acute symptomatic AF or paroxsysmal AF can be achieved by means of the use of antiarrhythmic drugs (AADs) or electrical cardioversion to restore sinus rhythm (SR). Alternatively, the physician may elect to simply control rate using drugs which slow AV node conduction and hence control ventricular response rate in patients with AF.

A large controversy currently exists as to whether rhythm control is superior to rate control of patients, although most opinion leaders would prefer their patients be in SR and have no need for anticoagulation. Studies evaluating incidence of serious cardiovascular (CV) sequeli or death with either approach are at this time inconclusive. Cardioversion by defibrillation is not a trivial undertaking, requiring patients to be sedated under the case of an anesthesiologist first and is associated with significant incidence of muscle pain and skin burns. Anti-arrhythmic drugs fall into a number of pharmacologic classes based on the mechanism of actions. There are five recognized AAD classes:

Class I: Na-channel blockers
Class II: Beta-blockers
Class III: K-channel blockers
Class IV: Ca-channel blockers
Class V: Miscellaneous (adenosine, digoxin, etc.)

The development of new anti-AF drugs has unfortunately, at this point, not increased the popularity of pharmacological cardioversion due to low efficacy rates, the risks of drug-induced torsades de pointes (TdeP), ventricular tachycardia, or other serious arrhythmias associated with currently available agents. Pharmacological cardioversion is still less effective than electrical cardioversion and, hence, defibrillation remains the mainstay of treatment of refractory acute atrial fibrillation.

Most marketed agents, e.g., propofenone, flecanide and ibutalide, carry risk of inducing TdeP; hence, most of these agents are not recommended for use in patients suffering from any of and having history of any of ischemic heart disease, prior MI, and prolonged QT syndrome. A number of these agents, such as sotalol, flecanide, propafenone and dronadarone, also display negative effects on contractility of the heart, making them contraindicated in heart failure. The most common severe adverse event is a pro-arrhythmic effect, which is usually associated with blockade of the human Ether-à-go-go-related gene (hERG)-encoded potassium channel $I_{Kr}$, resulting in QT-interval prolongation and potentially fatal ventricular arrhythmia TdeP. Notably, Na-channel blockers that lack inhibitory activity on $I_{Kr}$ also may be highly pro-arrhythmic (flecanide) in association with their ability to increase action potential duration, leading to Ca overload in a pronounced fashion and inducing re-entry rhythms.

Although anti-arrhythmic agents such as Na-channel blockers (Class I), Ca-channel blockers (Class IV) and beta-blockers (Class II), and digoxin and adenosine (Class V) all have some anti-AF properties, Class III anti-arrhythmic agents, which are all K-channel inhibitors and by recent consensus of medical experts mixed-channel blockers, are preferred for the anti-AF indication due to their perceived safety advantage and potency in atrial arrhythmia. Recurrent acute AF, persistent AF and paroxsysmal AF eventually lead to the development of chronic AF, there is electrical remodeling in atrial tissue, an adaptive response wherein the relative contributions of different atrial expressed ion channels change. This alteration in channel trafficking is manifested by the shortening of action potential (AP) duration, with a relatively greater contribution from the ultra rapid potassium current $I_{Kur}$, the transient outward potassium current $I_{to}$, and the muscarinic acetylcholine potassium current $I_{KAch}$, as well as a decreased influence of the delayed rectifying potassium current, which has two components: rapid [$I_{Kr}$] and slow [$I_{Ks}$]) and the calcium current. Chronic AF is intractable to medical intervention and maintaining SR in these patients is very difficult; leading to the statement that AF begets AF.

Currently available AADs that target potassium channels tend to block the late Phase 3 repolarizing currents, $I_{Kr}$ and $I_{Ks}$, which may make them less effective during AF because Phase 3 is shortened by chronic AF, although this hypothesis has not been proven with certainty. Currently available AADs also target the same ion channels in the ventricle, which can prolong the QT interval, resulting in enhanced risk of TdeP. AADs with selectivity for the atrial specific channels ($I_{Kur}$, $I_{to}$, $I_{KAch}$), which are more active after the electrical remodeling of AF, might provide effective rhythm control with minimal ventricular pro-arrhythmic risk, although down regulation of at least one of these atrial selective channels, $I_{KAch}$, has been reported with persistent/chronic AF.

Sulcardine, 4-methoxy-N-(3,5-bis-(1-pyrrolidinyl)-4-hydroxy benzyl)benzene sulfonamide, and its salts, such as sulcardine sulfate, constitute a group of new chemicals with potent anti-arrhythmic activity. Sulcardine is a multi-ion (fast and slow Na, L-Ca, and $K_{Ito}$) channel blocker and represents what may be the sole example of a substituted sulfonamide class of anti-arrhythmic. Sulcardine salts can be used as an intravenous injectable or as oral doses for the treatment of arrhythmias, including supraventricular tachyarrhythmia, premature ventricular contractions, ventricular tachycardia and ventricular fibrillation.

In addition, the evidence to date suggests that one advantage of sulcardine and salts is that they lack significant pro-arrhythmic activity, as demonstrated in rigorous preclinical safety models, including a post-MI sudden-death conscious canine model and the validated rabbit ventricular wedge model. Additionally, it has been shown that they do not increase defibrillation threshold, nor increase defibrillation failure risk in a post-MI canine model as was seen with flecanide. On the basis of these data, sulcardine and salts, with their very low apparent pro-arrhythmic potential, could potentially be used to treat acute and recurrent atrial fibrillation in the presence of organic heart disease, prolonged QR syndrome, and ventricular arrhythmias, including premature ventricular contractions (PVCs), ventricular tachycardia (VT), and ventricular fibrillation (VF), in either acute- or chronic-administration settings owing to their ability to be formulated into intravenous and oral dosing formulations.

SUMMARY OF THE INVENTION

It has been discovered that rapid intravenous or even short term infusion administration of sulcardine sulfate results in systemic diastolic and systolic hypotension and what is assumed to be a compensatory tachycardia, a hemodynamic effect not observed in either preclinical models or in humans with the oral administration of the agent, and that in dogs this hypotensive effect is due in part but not in whole to the release of histamine. This was illustrated by experiments in which administration of an anti-histamine, diphenhydrame, prior to IV administration of sulcardine sulfate was shown capable of blunting some of the cutaneous manifestations of histamine release (flushing and facial and ear edema) but only partially reversed the hypotension seen on dosing. Other animals models (primate, minipig) also display hypotension upon intravenous administration of sulcardine sulfate (data not presented) and do so without detectable release of histamine into the blood stream, further supporting the fact that hypotension caused, by rapid IV administration of sulcardine sulfate occurs in the absence of allergic reaction and is likely associated with the drug's effect to block Ca ion channels in vascular smooth muscle.

By means of a post myocardial infarction sudden death dog model, it was discovered that drug infusion rate was inversely proportional to this hypotensive response, and that slower infusion rates, in the range of greater than 15 minutes prevented hypotension after IV dosing in the dog. These data indicate that the side effects are related to the high plasma concentration of sulcardine sulfate seen in the immediate post administration period.

The goal of pharmacologic therapy for the treatment of AF depends on whether one is treating acute or paroxysmal AF, to induce rapid cardioversion to a normal sinus rhythm, or whether one seeks to prevent AF recurrence with prolonged administration of the drug. In acute or paroxysmal AF in patients who do not have a history of frequent recurrence, the goal it to acutely induce the pharmacologic cardioversion of a patient who currently is suffering from an AF episode, typically with the administration of a single drug dose or with administration of a limited number of doses. Alternatively, prevention of recurrent AF episodes requires chronic prophylactic treatment.

It has been discovered that, in the context of treating acute or paroxysmal AF to induce immediate cardioversion, the efficacy of sulcardine and its pharmaceutically acceptable salts is a function of peak plasma concentration, requiring the maintenance of a high plasma level for a minimal period, for example, of minutes to less than one hour in duration, to afford time for cardioversion to a normal sinus rhythm; after that time, the patient should remain in normal sinus rhythm without the need for continued therapeutic plasma levels of drug, unless some other precipitating event causes a future recurrence of the arrhythmia. These types of patients who have no or only limited prior history of AF episodes have lower risk of recurrence; hence, continued drug therapy following cardioversion is not indicated. For the acute or paroxysmal AF indication, it is unnecessary to maintain steady blood levels of the drug (steady drug concentration area under the plasma-time curve) for prolonged periods of time, to prevent recurrence of AF over days to months to years at a time. The use of the drug in this clinical situation is akin to the use of electrical cardioversion to acutely drive the heart back into a normal sinus rhythm.

It also has been discovered that the efficacy of sulcardine and its pharmaceutically acceptable salts in the treatment of patients with persistent or frequently recurring AF is a function of the area under the plasma-time curve, rather than of a peak plasma concentration. These patients, with a significant history of prior AF and frequent recurrence, are at much higher risk of recurrence that the acute cohort described above. The atria appear to remodel following frequent or prolonged (chronic) AF episodes, predisposing the patient to a higher risk of future events. As the clinicians say; AF begets AF.

Prevention of recurrent AF in such chronic AF patients requires maintaining drug concentration peak and trough concentrations over the dosing period within a range that minimizes the risk of adverse events, associated with high plasma concentrations, and yet that maintains blood levels above some minimally pharmacologically active concentration. Accordingly, in the treatment of both acute/paroxysmal and recurrent AF, administering active agent over a longer period, e.g., by means of a controlled release formulation or by slow intravenous infusion, has a role to play. In the acute/paroxysmal AF medical setting, the goal is to achieve rather high blood levels for a period of minutes out to an hour or two, allowing the heart sufficient time to respond to drug therapy and slip back into a normal sinus rhythm. Loading the drug by a continuous, short-term infusion over this period, as opposed to administering the drug by a rapid IV push, blunts peak plasma concentrations, minimizing the risk of hypotension, while allowing for the achievement of high blood levels over a period of time sufficient to result in cardioversion.

In accordance with one aspect of the invention, therefore, a method is provided for administering to a subject a composition comprised of an active agent that is 4-methoxy-N-(3, 5-bis-(1-pyrrolidinyl)-4-hydroxy benzyl)benzene sulfonamide (sulcardine) or a pharmaceutically acceptable salt thereof. The inventive, method comprises intravenously administering the composition substantially evenly to the subject over a period of greater than about 15 minutes. The period in question may be from about 30 minutes to about 180 minutes, from about 30 minutes to about 120 minutes, from about 30 minutes to about 60 minutes, or may be about 45 minutes.

The invention also contemplates administering a composition comprised of an active agent, which is 4-methoxy-N-(3,5-bis-(1-pyrrolidinyl)-4-hydroxy benzyl) benzene sulfonamide (sulcardine) or a pharmaceutically acceptable salt thereof, substantially evenly to a subject. In this manner, pursuant to the invention, no more than about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, or no more than about 1 mg/kg of the active agent is administered to said subject per minute.

Also provided are methods of treating arrhythmia with these administration methods.

BRIEF DESCRIPTION OF THE DRAWINGS

FIG. 1 shows hemodynamic effects of a 45 minute intravenous sulcardine sulfate infusion administered to anesthetized dogs in the sudden death model. Times on X axis represent time after completion of 45 minute drug infusion.

DETAILED DESCRIPTION OF THE INVENTION

Throughout this application, the text refers to various embodiments of the inventive compounds, compositions, and methodology. The various embodiments described are representative only and should not be construed as descriptions of alternative species. Rather, the descriptions provided here may be of overlapping scope. The embodiments discussed are illustrative only and are not meant to limit the scope of the present invention.

I. Definitions

Unless indicated otherwise, the terms and phrases used in this description have the following meanings:

"Treat," "treatment," and "treating" are employed in this description to refer to administering a pharmaceutical composition or formulation for prophylactic and/or therapeutic purposes. The term "therapeutic treatment" refers to administering treatment to a patient already suffering from a condition such as arrhythmia. Thus, in preferred embodiments, treating is the administration to a mammal of therapeutically effective amounts of an anti-arrhythmic agent.

A "subject" of treatment is a prokaryotic or a eukaryotic cell, a tissue culture, a tissue or an animal, e.g., a mammal, including a human. Non-human animals subject to treatment include, for example, a simian, a murine, a canine, a leporid, such as a rabbit, livestock, sport animals, and pets.

An "anti-arrhythmic agent," as used herein, refers to a molecule having a therapeutic effect of treating arrhythmia or alleviating associated symptoms in a subject. Non-limiting examples of arrhythmias include supraventricular tachyarrhythmia, premature ventricular contractions, ventricular tachycardia, and ventricular fibrillation. In one aspect, an anti-arrhythmic agent is 4-methoxy-N-(3,5-bis-(1-pyrrolidinyl)-4-hydroxy benzyl)benzene sulfonamide (sulcardine) or a pharmaceutically acceptable salt thereof. In another aspect, an anti-arrhythmic agent is sulcardine sulfate.

In accordance with this invention, a pharmaceutically acceptable salt of sulcardine, 4-methoxy-N-(3,5-bis-(1-pyrrolidinyl)-4-hydroxy benzyl)benzene sulfonamide, can be the active agent in a formulation useful for treating arrhythmia. Illustrative of such sulcardine salts are: (A) inorganic acid salts such as acetate, borate, bicarbonate, sulfate, hydrochloride, bromides, chlorides, iodide, hydrobromide, hydroiodide, nitrate, phosphate, diphosphate, and fluorophosphate salts; (B) organic acid salts such as amsonate (4,4-diaminostilbene-2,2-disulfonate), bitartrate, butyrate, citrate, calcium edetate, camsylate, edisylate, estolate, esylate, glutamate, gluconate, gluceptate, lactate, lactobionate, laurate, malate, maleate, mandelate, methylbromide, methylnitrate, methylsulfate, mucate, oleate, oxalate, palmitate, pamoate (1,1-methene-bis-2-hydroxy-3-naphthoate, einbonate), pamoate, pantothenate, salicylate, stearate, subacetate, succinate, sulfate, sulfosalicylate, suramate, propionate, valerate, fiunarate, fumarate, and tartrate salts; and (C) alkali metal salts and alkali earth salts, such as the sodium, potassium, lithium and calcium salts of sulcardine. In this context, a pharmaceutically acceptable salt can have more than one charged atom in its structure and, hence, one or more counterions.

The phrases "effective amount," "therapeutically effective amount," and "pharmaceutically effective amount" denote an amount of an active agent, such as an anti-arrhythmic agent as presently disclosed, that has a therapeutic effect. The doses of the active agent which are useful in treatment are therapeutically effective amounts. Thus, a therapeutically effective amount is an amount of the active agent that produces the desired therapeutic effect, as judged by clinical trial results and/or model animal studies. In particular embodiments, the active agent is administered in a pre-determined dose; hence, a therapeutically effective amount would be an amount of the dose administered. This amount and the amount of the anti-arrhythmic agent can be determined routinely, by conventional methodology, and will vary as a function of different factors, such as the particular arrhythmic event involved. This amount also can depend upon the patient's height, weight, sex, age and medical history.

A "carrier" or "excipient" is a compound or material used to facilitate administration of the compound, for example, to control the release and/or bioavailability of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); GOODMAN AND GILMAN'S: THE PHARMACOLOGICAL BASIS OF THERAPEUTICS, 8th Ed., Pergamon Press.

The phrases "pharmaceutically acceptable carrier" and "pharmaceutically acceptable excipient" can note any and all solvents, dispersion media, coatings, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. Suitable pharmaceutically acceptable excipients include, but are not limited to, buffers, diluents, tonicity agents, stabilizers, antioxidants, preservatives and mixtures thereof.

The term "buffer" denotes a pharmaceutically acceptable excipient, which stabilizes the pH of a pharmaceutical preparation. Suitable buffers are well known in the art and can be found in the literature. Pharmaceutically acceptable buffers comprise but are not limited to glycine-buffers, histidine-buffers, citrate-buffers, succinate-buffers and phosphate-buffers. Independently from the buffer used, the pH can be adjusted at a value from about 2 to about 9, or alternatively from about 2.5 to about 7, or alternatively from about 3 to about 4 or alternatively about 3 with an acid or a base known in the art, e.g., succinic acid, hydrochloric acid, acetic acid, phosphoric acid, sulfuric acid and citric acid, sodium hydroxide and potassium hydroxide. Suitable buffers include, without limitation, glycine buffer, histidine buffer, 2-morpholino-ethanesulfonic acid (MES), cacodylate, phosphate, acetate, succinate, and citrate. In one aspect, the buffer is a glycine buffer. In another aspect, the buffer is a histine buffer. The concentration of the buffer can be between about 1 mM and about 100 mM, or alternatively about 2 mM to about 40 mM, or alternatively about 5 mM to about 20 mM.

The terms "diluent," "filler," "dilutant" and "thinner" refer to an inactive ingredients that are added to tablets or capsules in addition to the active drug. A diluent may be used as binders, disintegrants (help the tablet break apart in the digestive system), or flavor enhancers. In one aspect, a diluent is solid, such as starch, cellulose derivatives, and magnesium stearate. In another aspect, a diluent is liquid, such as water, saline, and a dextrose solution (e.g., 5%).

The phrase "tonicity agent" denotes the category of pharmaceutically acceptable agents used to modulate the tonicity of the formulation. Isotonicity generally relates to the osmotic pressure relative to a solution, usually relative to that of human blood serum. A formulation can be hypotonic, isotonic or hypertonic. In one aspect, the formulation is isotonic. An isotonic formulation is liquid or liquid reconstituted from a solid form, e.g., from a lyophilized form and denotes a solution having the same tonicity as some other solution with which it is compared, such as physiologic salt solution and the blood serum. Suitable isotonicity agents include but are not limited to sodium chloride, potassium chloride, mannitol, sucrose, glycerin and any component from the group of amino acids, sugars, as defined herein as well as combinations thereof. In some embodiments, mannitol is present in a concentration of from about 1% to about 20% (w/v %), or alternatively from about 2% to about 10% or alternatively from about 2.5% to about 5%. In one aspect, mannitol is present at about 3%.

The term "stabilizer" denotes a pharmaceutical acceptable excipient, which protects the active pharmaceutical ingredient and/or the formulation from chemical and/or physical degradation during manufacturing, storage and application. Stabilizers include but are not limited to sugars, amino acids, polyols, surfactants, antioxidants, preservatives, cyclodextrines, e.g., hydroxypropyl-β-cyclodextrine, sulfobutylethyl-β-cyclodextrin, β-cyclodextrin, polyethyleneglycols, e.g., PEG 3000, 3350, 4000, 6000, albumin, e.g., human serum albumin (HSA), bovine serum albumin (BSA), salts, e.g., sodium chloride, magnesium chloride, calcium chloride, chelators, e.g., EDTA. In one aspect, a stabilizer is selected from the group consisting of soldium sulfite, sodium bisulfate, sodium metabisulfate, ascordib acid, sodium chloride, EDTA, dextrose, sorbitol, polyethylene glycol (PEG), glycerol and combinations thereof.

In the present context, the term "surfactant" refers to a pharmaceutically acceptable organic substance having amphipathic structures; namely, it is composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials. In some embodiments of the pharmaceutical formulations described herein, the amount of surfactant is described a percentage expressed in weight/volume percent (w/v %). Suitable pharmaceutically acceptable surfactants include but are not limited to the group of polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), or sodium dodecyl sulphate (SDS). Polyoxyethylenesorbi-tan-fatty acid esters include polysorbate 20, (sold under the trademark Tween 20™) and polysorbate 80 (sold under the trademark Tween 80™). Polyethylene-polypropylene copolymers include those sold under the names Pluronic© F68 or Poloxamer 188™. Polyoxyethylene alkyl ethers include those sold under the trademark Brij™. Alkylphenolpolyoxyethylene ethers include those sold under the tradename Triton-X. When polysorbate 20 (Tween 20™) and polysorbate 80 (Tween 80™).

An "antioxidant" refers to a molecule capable of slowing or preventing the oxidation of other molecules. Oxidation is a chemical reaction that transfers electrons from a substance to an oxidizing agent. Oxidation reactions can produce free radicals, which start chain reactions that destabilize the product therapeutics and ultimately affect the product activity. Antioxidants terminate these chain reactions by removing free radical intermediates, and inhibit other oxidation reactions by being oxidized themselves. As a result, antioxidants are often reducing agents, chelating agent and oxygen scavengers such as thiols, ascorbic acid or polyphenols. Non-limiting examples of antioxidants include ascorbic acid (AA, E300), thiosulfate, methionine, tocopherols (E306), propyl gallate (PG, E310), tertiary butylhydroquinone (TBHQ), butylated hydroxyanisole (BHA, E320) and butylated hydroxytoluene (BHT, E321).

A "preservative" is a natural or synthetic chemical that is added to products such as foods, pharmaceuticals, paints, biological samples, wood, etc. to prevent decomposition by microbial growth or by undesirable chemical changes. Preservative additives can be used alone or in conjunction with other methods of preservation. Preservatives may be antimicrobial preservatives, which inhibit the growth of bacteria and fungi, or antioxidants such as oxygen absorbers, which inhibit the oxidation of constituents. Common antimicrobial preservatives include, benzalkonium chloride, benzoic acid, cholorohexidine, glycerin, phenol, potassium sorbate, thimerosal, sulfites (sulfur dioxide, sodium bisulfite, potassium hydrogen sulfite, etc.) and disodium EDTA.

II. Slow Intravenous Infusion

It was an unexpected finding related to the invention that the rapid intravenous or even short-term infusion administration of sulcardine sulfate results in systemic diastolic and systolic hypotension and what is believed to be a compensatory tachycardia, a hemodynamic effect not observed in either preclinical models or in humans with the oral administration of the agent. In dogs, moreover, this hypotensive effect was due in part but not in whole to the release of histamine. This was illustrated by experiments in which administration of an anti-histamine (diphenhydrame) prior to IV administration of sulcardine sulfate is capable of blunting some of the cutaneous manifestations of histamine release (flushing and facial and ear edema), but only partially reversed the hypotension seen on dosing. Other animals models (e.g., primate, minipig) also displayed hypotension upon intravenous administration of sulcardine sulfate as well (data not presented) and do so without detectable release of histamine into the blood stream, further supporting the conclusion that hypotension caused by rapid IV administration of sulcardine sulfate occurs in the absence of allergic reaction and is likely associated with the drug's effect to block Ca ion channels in vascular smooth muscle, By means of a post-myocardial infarction sudden death dog model, it was discovered that drug infusion rate was inversely proportional to this hypotensive response, and that slower infusion rates, in the range of greater than 15 minutes, for example, 45 minutes or longer, completely prevented the observation of hypotension after IV dosing in the dog. These data suggest that the side effects are related to the high plasma concentration of sulcardine sulfate after administration.

It has been discovered as well that the efficacy of sulcardine and its pharmaceutically acceptable salts is associated with the area under the plasma-time curve, rather than being due to a signal transduction-triggering event associated with a peak plasma concentration. Therefore, a slow administration of sulcardine or one of its pharmaceutically acceptable salts will lead to lower maximum plasma concentration, which in turn will reduce or prevent side effects while maintaining efficacy.

Accordingly, the invention provides a method of administering to a subject a composition comprised of an active agent that is 4-methoxy-N-(3,5-bis-(1-pyrrolidinyl)-4-hydroxy benzyl)benzene sulfonamide (sulcardine) or a pharmaceutically acceptable salt thereof, the method comprising intravenously administering said composition substantially evenly to said subject over a period of greater than about 15 minutes. The period in question may be from about 30 minutes to about 180 minutes, from about 30 minutes to about 120 minutes, from about 30 minutes to about 60 minutes, or may be about 45 minutes.

"Substantially evenly" is employed here to denote administering to a subject a similar amount of an active agent per time unit over the whole course of administration. In one aspect, the maximum amount of the active agent administered per minute during the course of administration is not more than about 100% greater than the average amount of the active agent administered per minute. Alternatively, this figure can be about 75% or about 50% of the average amount administered per minute. In another aspect, the minimum amount of the active agent administered per minute during the course of administration is not lower than about 50%, not lower than about 65%, or not lower than about 75% of the average amount of the active agent administered per minute. In yet another aspect, the amount of the active agent administered per minute during the course of administration is characterized by an average value and a standard deviation, where the latter is not greater than about 100%, not greater than about 75%, or not greater than about 50% of the average. Pursuant to the invention, moreover, the infusion can be restricted significantly or can be stopped for a period of time without necessitating rapid infusion during another time of the administration.

Also provided is a method of administering to a subject a composition comprised of an active agent that is 4-methoxy-N-(3,5-bis-(1-pyrrolidinyl)-4-hydroxy benzyl)benzene sulfonamide (sulcardine) or a pharmaceutically acceptable salt thereof, the method comprising intravenously administering said composition to said subject, wherein no more than about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, or alternatively no more than about 1 mg/kg, of said active agent is administered to said subject per minute.

In one aspect of the above embodiments of the invention, the amount of the active agent administered is lower than about 90 mg/kg, or alternatively lower than about 80 mg/kg, about 70 mg/kg, about 60 mg/kg, about 50 mg/kg, about 40 mg/kg, about 30 mg/kg, about 20 mg/kg, about 10 mg/kg, about 9 mg/kg, about 8 mg/kg, about 7 mg/kg, about 6 mg/kg, about 5 mg/kg, about 4 mg/kg, about 3 mg/kg, about 2 mg/kg, about 1 mg/kg, about 0.7 mg/kg, about 0.5 mg/kg, about 0.3 mg/kg, about 0.2 mg/kg or 0.1 mg/kg. In another aspect, the amount of the active agent administered is from about 0.1 mg/kg to about 90 mg/kg, from about 0.5 mg/kg to about 80 mg/kg, from about 1 mg/kg to about 70 mg/kg, from about 3 mg/kg to about 30 mg/kg, or alternatively from about 10 mg/kg to about 30 mg/kg.

The amount of the active agent administered will depend in part on the characteristics of the subject, including without limitation the species, gender and age of the subject. Various mathematical algorithms exist for effecting a conversion of administered amounts, e.g., between different species, as described, for instance in GUIDANCE OF INDUSTRY—ESTIMATING THE MAXIMUM SAFE STARTING DOSE IN INITIAL CLINICAL TRIALS FOR THERAPEUTICS IN ADULT HEALTHY VOLUNTEERS, U.S. Department of Health and Human Services, Food and Drug Administration, Center for Drug Evaluation and Research (July 2005), accessible at wwwfda.gov/Drugs/GuidanceCompliance-RegulatoryInformation/Guidances/ucm065014.htm. Thus, 1 mg/kg of the active agent in dog is equivalent to about 0.54 mg/kg in human, and 0.3 mg/kg of the active agent in dog is equivalent to about 0.16 mg/kg in human.

As noted above, the active agent of a formulation of the invention can be a pharmaceutically acceptable salt of sulcardine, 4-methoxy-N-(3,5-bis-(1-pyrrolidinyl)-4-hydroxy benzyl)benzene sulfonamide. The preparation of such salts is illustrated by way of the reaction chemistries described below.

1. Reaction of Sulcardine with an Organic or Inorganic Acid

Amines, such as the tertiary amine $R_3N$, react with strong inorganic acids such as hydrochloric acid, hydrobromic acid or hydroiodic acid, to give the corresponding ammonium salt $R_3NH^+ X^-$, where X is Cl, Br, or I. Generally, this reaction is carried out by dissolving the amine in an aqueous solvent followed by the addition of a slight excess of the strong acid to the amine. In a typical protocol, sulcardine is dissolved in an aqueous or aqueous-alcoholic solvent, which then is cooled by placing the flask in an ice bath. To the cold stirring solution is added drop-wise a slight excess of the strong acid. After the addition of the acid, the reaction mixture is brought to room temperature and concentrated to precipitate the corresponding salt, which can be separated by filtration. The addition of around 1.1 equivalents of a strong acid results in the formation of a mono-salt of sulcardine, while the bis salt is readily obtained by the addition of around 2.1 equivalents of a strong acid.

Organic acid salts of sulcardine, such as an acetate salt, can be synthesized by passing the compound through a reverse-phase, high-pressure liquid chromatography column, using an aqueous-organic solvent system, such as a water-methanol or water-acetonitrile solvent system that contains 1.0 to 2.0 equivalents of acetic acid. As a result, the mono- and bis salts of sulcardine are formed. See Streitwiesser et al., INTRODUCTION TO ORGANIC CHEMISTRY 4$^{th}$ ed. (Macmillan Publishing Co.), at page 736.

2. Reaction of Sulcardine with an Alkyl Halide

In generally, quaternary ammonium halides can be prepared by reacting an alkyl or an araalkyl halide with an appropriate tertiary amine in a non-reactive organic solvent. By the same token, sulcardine could be reacted with an alkyl bromide or alkyl iodide in ether or tetrahydrofuran, at room temperature, to form corresponding methyl salts via the formation of a methylpyrrolidinium cation. The stoichiometry of alkyl halide in the reaction would dictate the type of salt formed. Thus, adding 1.0 mole of an alkyl halide would give the mono corresponding pyrrolidinyl methyl salt, while the addition of 2.0 moles of an alkyl halide would allow for the formation of the bis salt. See Streitwiesser et al., supra, at page 737.

3. Formation of Alkali Metal Salts of Sulcardine

Synthesis of alkali metal salts of sulcardine entails use of a strong base to effect abstraction of the —NH proton of sulfonamide. Accordingly, the addition of sodium hydride to a cold, rapidly stirring solution of sulcardine in an aprotic anhydrous solvent, such as anhydrous tetrahydrofuran, should result in the formation of a sodium salt as represented in Formula I:

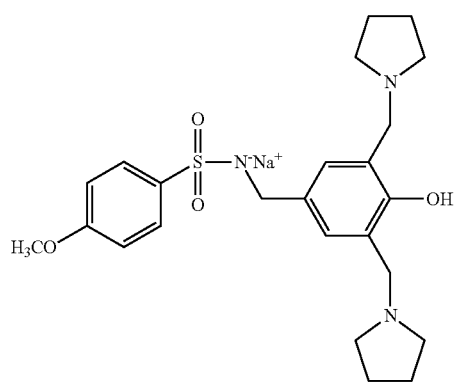

I

See Singh et al., BIOORGANIC & MED. CHEM. LETTERS 16: 3921-26 (2006).

The reaction would be carried out by the drop-wise addition of a tetrahydrofuran solution of sodium hydride to a cold, round-bottom flask, which contains a solution of sucradine. After completing the addition of the sodium hydride, the reaction would be warmed to room temperature and stirred. The reaction would be complete when no more hydrogen gas is evolved.

In some embodiments, the composition further comprises a pharmaceutically acceptable excipient or carrier or other agents. The amount of the active agent in the Composition can vary within the full range employed by those skilled in the art. Typically, the composition will contain, on a weight percent (wt %) basis, from about 0.01-99.99 wt % of the active agent based on the total formulation, with the balance being one or more suitable pharmaceutical excipients. Preferably, the active agent is present at a level of about 1-80 wt %.

Pharmaceutically acceptable excipients suitable for carrying out the invention include, buffers, diluents, tonicity agents, stabilizers, antioxidants, preservatives and mixtures thereof.

Suitable buffers include, without limitation, glycine buffer, histidine buffer, 2-morpholinoethanesulfonic acid (MES), cacodylate, phosphate, acetate, succinate, and citrate. In one aspect, the buffer is a glycine buffer. In another aspect, the buffer is a histidine buffer. The concentration of the buffer can be between about 1 mM and about 100 mM, or alternatively about 2 mM to about 40 mM, or alternatively about 5 mM to about 20 mM.

In some embodiments, the diluents is water, saline or 5% dextrose.

In some embodiments, the pharmaceutically acceptable excipient is a stabilizer. In one aspect, the stabilizer is selected from the group consisting of sorbitol, EDTA and glycerol. In another aspect, the stabilizer is sorbitol present at about 3% concentration in the composition. In yet another aspect, the stabilizer is EDTA present at about 0.05% concentration in the composition. In further another aspect, the stabilizer is glycerol present at about 2% concentration in the composition.

III. Therapies

The present invention, in another aspect, provides a method for treating a subject in need of therapy, comprising administering to said subject a composition comprised of an active agent that is 4-methoxy-N-(3,5-bis-(1-pyrrolidinyl)-4-hydroxy benzyl)benzene sulfonamide (sulcardine) or a pharmaceutically acceptable salt thereof, the method comprising intravenously administering said composition substantially evenly to said subject over a period of greater than about 15 minutes. The period in question may be from about 30 minutes to about 180 minutes, from about 30 minutes to about 120 minutes, from about 30 minutes to about 60 minutes, or may be about 45 minutes.

Also provided is a method for treating a subject in need of therapy, comprising administering to said subject a composition comprised of an active agent that is 4-methoxy-N-(3,5-bis-(1-pyrrolidinyl)-4-hydroxy benzyl)benzene sulfonamide (sulcardine) or a pharmaceutically acceptable salt thereof, the method comprising intravenously administering said composition to said subject, wherein no more than about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, or alternatively no more than about 1 mg/kg, of said active agent is administered to said subject per minute.

In one aspect of the above embodiments of the invention, the amount of the active agent administered is lower than about 90 mg/kg, or alternatively lower than about 80 mg/kg, about 70 mg/kg, about 60 mg/kg, about 50 mg/kg, about 40 mg/kg, about 30 mg/kg, about 20 mg/kg, about 10 mg/kg, about 9 mg/kg, about 8 mg/kg, about 7 mg/kg, about 6 mg/kg, about 5 mg/kg, about 4 mg/kg, about 3 mg/kg, about 2 mg/kg, about 1 mg/kg, about 0.7 mg/kg, about 0.5 mg/kg, about 0.3 mg/kg, about 0.2 mg/kg or 0.1 mg/kg. In another aspect, the amount of the active agent administered is from about 0.1 mg/kg to about 90 mg/kg, from about 0.5 mg/kg to about 80 mg/kg, from about 1 mg/kg to about 70 mg/kg, from about 3 mg/kg to about 30 mg/kg, or alternatively from about 10 mg/kg to about 30 mg/kg.

In some embodiments, the subject suffers from or is at risk of suffering from arrhythmia. Non-limiting examples of arrhythmias include supraventricular tachyarrhythmia, premature ventricular contractions, ventricular tachycardia, ventricular fibrillation and atrial fibrillation (VF). In one aspect, the subject suffers from or is at risk of suffering from VF.

Pharmaceutically acceptable excipients suitable for carrying out the invention include, buffers, diluents, organic co-solvents, tonicity agents, stabilizers, antioxidants, preservatives and mixtures thereof.

Suitable buffers include, without limitation, glycine buffer, histidine buffer, 2-morpholinoethanesulfonic acid (MES), cacodylate, phosphate, acetate, succinate, and citrate. In one aspect, the buffer is a glycine buffer. In another aspect, the buffer is a histidine buffer. The concentration of the buffer can be between about 1 mM and about 100 mM, or alternatively about 2 mM to about 40 mM, or alternatively about 5 mM to about 20 mM.

In some embodiments, the diluents is water, saline or 5% dextrose.

In some embodiments, the pharmaceutically acceptable excipient is a stabilizer. In one aspect, the stabilizer is selected from the group consisting of sorbitol, EDTA and glycerol. In another aspect, the stabilizer is sorbitol present at about 3% concentration in the composition. In yet another aspect, the stabilizer is EDTA present at about 0.05% concentration in the composition. In further another aspect, the stabilizer is glycerol present at about 2% concentration in the composition.

A formulation of the present invention can be administered by methods known in the art. It will also be appreciated that the preferred route will vary with the condition and age of the recipient, and the disease being treated. Methods of determining the most effective means and dosage of administration are known to those of skill in the art and will vary with the composition used for therapy, the purpose of the therapy, and the subject being treated. Single or multiple administrations can be carried out with the dose level and pattern being selected by the treating physician. Suitable dosage formulations and methods of administering the agents are known in the art.

The effective amount of the formulation of the invention can be experimentally determined and can vary depending upon the specific formulation, the disease or symptom to be treated or alleviated, the age, gender and weight of the subject to be treated, the dosing regimen of the formulation, the severity of the disease condition, the manner of administration and the like, all of which can be determined readily by one of skill in the art.

Administration of the formulation of the invention can be composed of one dose, or a number of consecutive doses. The amount and frequency of dosage can be determined with methods known in the art, and will vary depending on factors such as the risk of continued risk, half life of the active ingredient and toxicity of the formulation.

Administration of the formulation of the invention can be made at one site of the subject, or multiple sites of the subject. The amount of dosage and sites can be determined with methods known in the art.

The subject suitably treated by the methods and formulation of the invention can be a mammal including a human. Non-human animals subject to treatment include, for example, a simian, a murine, a canine, a leporid, such as a rabbit, livestock, sport animals, and pets.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Example 1

Administration Rate-Dependent Hemodynamic Effects

The effect of sulcardine sulfate intravenously administered over a 10 minute infusion on the mean blood pressure, heart rate, and plasma histamine concentration of conscious beagle dogs was performed. Three male and female purpose-bred beagles, weighing 10.0-12.7 Kg were intravenously administered repeated increasing doses of sulcardine sulfate (cumulative dose 1-44 mg/kg) at 15 minute intervals following a 10 minute infusion of the prior dose. The administered doses were as follows: 1 mg/kg, 3 mg/kg, 10 mg/kg, and 30 mg/kg sulcardine sulfate. Heart rate, mean arterial blood pressure, and histamine concentrations were measured (Table 1) at 10 minute intervals after completion of each drug infusion period.

TABLE 1

Data Summary of Sulcardine Sulfate on Hemodynamics

| | Pretreatment | Sulcardine Sulfate Dose | | | |
| --- | --- | --- | --- | --- | --- |
| | | 1 mg/kg | 3 mg/kg | 10 mg/kg | 30 mg/kg |
| Heart rate (bpm) | 80.00 ± 7.64 | 90.00 ± 12.58 | 110.00 ± 10.41 | 111.7 ± 17.64 | 111.7 ± 6.01 |
| Mean blood pressure (mmHg) | 167.7 ± 10.97 | 166.7 ± 10.99 | 170.7 ± 7.36 | 101.0 ± 28.45 | 69.7 ± 14.7* |
| Histamine Concentration (ng/mL) | 86.64 ± 10.63 | 93.95 ± 24.11 | 182.5 ± 46.11 | 252.6 ± 85.78 | 465.9 ± 27.75* |

During the course of the study it was observed that the intravenous administration of sulcardine sulfate over 10 minutes was associated with a dose-dependent decrease in arterial blood pressure that was accompanied by the appearance of an erythemitous flare in the region of the face and ears plus the appearance of urticaria (hives). The effect became less intense with successive injections, most likely due to the depletion of mast cell stores of histamine. Pretreatment with diphenhydramine (H1 histamine receptor antagonist) or lodoxamide (mast cell inhibitor) prevented the histamine-mediated events. The dose dependent increase in plasma histamine concentrations was determined by an ELISA assay.

Three additional animals received sulcardine sulfate (14 mg/kg, i.v.) infused over 45 minutes. The purpose of this study was to investigate whether or not a slow infusion (45 min) of sulcardine sulfate would affect heart rate, and blood pressure. The results are summarized in Table 2. The data show a progressive increase in the resting heart rate during infusion. The change in blood pressure was modest, most likely due to a compensatory increase in the resting heart rate. Thus, the slow intravenous administration of sulcardine sulfate in a total intravenous dose of 14 mg/kg did not result in a marked change in resting blood pressure and/or heart rate as observed with bolus injection.

TABLE 2

Effects of Sulcardine Sulfate (14 mg/kg) on Heart Rate and Blood Pressure over 45 minutes of Infusion

| | Time (minutes) | | | | |
|---|---|---|---|---|---|
| | 0 | 10 | 25 | 40 | 55 |
| Heart rate (bpm) | 73.3 ± 3.3 | 95.0 ± 7.6 | 115.0 ± 5.8* | 115.0 ± 5.0* | 103.3 ± 6.0 |
| Mean blood pressure (mmHg) | 168.7 ± 5.2 | 165.3 ± 0.3 | 167.7 ± 9.8 | 162.7 ± 11.3 | 152.0 ± 16.2 |

N = 3;
*P < 0.05 vs. 0 Minutes, Repeated Measures ANOVA

A hemodynamic effects study of sulcardine sulfate in an anesthetized post-MI sudden cardiac death model study was also performed. The study population consisted of ten purpose-bred, female beagle dogs, weighing 10.0-12.0 Kg. The animals had left ventricular wall ischemic injury induced by a 90-minute occlusion of the left anterior descending coronary artery followed by reperfusion. Five animals were treated with sulcardine sulfate (15 mg/kg) infused intravenously over 10 minutes, and the remaining five animals were vehicle dogs treated with 0.9% sodium chloride solution (placebo). Lowest mean arterial blood pressure was measured every 15 minutes for a total period of 120 minutes after treatment. The results are summarized in FIG. 1.

The mean arterial blood pressures at fifteen, thirty, and forty-five minutes after completing a 10 minute infusion of sulcardine sulfate (15 mg/kg) were significantly lower compared to sulcardine sulfate baseline values (P<0.05, Repeated Measures ANOVA). The mean arterial blood pressure in vehicle animals did not change significantly over time. P<0.05 Placebo vs sulcardine sulfate using Two Way ANOVA. Upon completion of the min sulcardine sulfate infusion, there was a gradual and progressive return of the arterial blood pressure that was not different from pre-drug baseline or the placebo treated animals by 50 minutes following completion of drug infusion.

Example 2

Hemodynamic Effects of Short Term Infusion of Sulcardine Sulfate When Combined with Diphenhydramine Pretreatment in Anesthetized Dogs Dogs were administered morphine (2 mg/kg subcutaneously) approximately 10-19 minutes prior to administration of anesthesia. Dogs were anesthetized with 1% α-chloralose (100 mg/kg intravenous), followed by a constant infusion of α-chloralose (35-75 mg/kg/hr, IV). Two healthy female dogs were administered escalating doses of sulcardine sulfate intravenously over 15 minutes in an acetate buffer system at dose levels of 10, 30 and 90 mg/kg with dose administrations separated by 60 minutes. Another set of two dogs received test article after pre-treatment with diphenhydramine (1 mg/kg administered 30 minutes prior to start of test article infusion). Following drug administration, dogs were evaluated for ventricular, pulmonary and peripheral hemodynamic changes using Swanz Ganz and femoral catheters as well as by monitoring of blood oxygen saturation, test article blood level, body temperature, blood biochemistry, hematology, ECG, and histamine levels.

Hemodynamic Results

Group 1 (Sulcardine sulfate at 10, 30 and 90 mg/kg). Hemodynamic effects were observed with all doses of sulcardine sulfate. During the initial infusion of sulcardine sulfate in dogs not pre-treated with diphenhydramine at 10 mg/kg, the changes included marked increases in heart rate (HR) (+194% to +271%) and contractility (+96% to +109%). Left ventricular end diastolic pressure (LVEDP) displayed an initial increase immediately post dosing followed by a pronounced decrease (−157% to −710%). Mean pulmonary arterial pressure (MPAP) (+35% to +76%) and cardiac output (CO) (+80 to 131%) were also increased after sulcardine sulfate administration at 10 mg/kg. During the same period, an initial increase (+66%) in mean arterial pressure was observed in one animal out of two which attained its maximum at 10 minutes post start of dosing. However, both animals eventually displayed a decreased in mean arterial pressure (MAP) in the post-dose period (−33% to −41%). Maximal effects were observed at approximately 10 minutes into the infusion and returned gradually toward baseline at the end of the 60 minutes monitoring period with the exception of HR, contractility and LVEDP which remained elevated throughout the monitoring period. Similar hemodynamic changes were observed with the initiation of the second infusion (30 mg/kg) with the exception of HR and contractility which slightly decreased during dosing up to the end of the infusion followed by an increase after dosing was completed. At 90 mg/kg, all animals succumbed at the completion of the final 15-minute infusion where cardiac depression leading to severe hypotension was present.

Group 2 Animals: Sulcardine sulfate at 10, 30 and 90 mg/kg with diphenhydramine (1 mg/kg) administered approximately 30 minutes before treatment with 10 mg/kg sulcardine sulfate. Animals pre-treated with diphenhydramine (H1 antagonist) and dosed with sulcardine sulfate at 10 mg/kg, presented hemodynamic changes that are mediated by H2 receptors.

The changes resembled those noted in Group 1 animals, but were of a reduced magnitude. Changes included marked increases of heart rate (HR) (+124% to +157%) however not sustained, and contractility (+41% to +58%), mean pulmonary arterial pressure (MPAP) (+30% to +57%) and Cardiac output (CO) (+108 to 184%) with a slight decreased mean arterial pressure MAP (−12% to −17%). Left ventricular end diastolic pressure (LVEDP) which displayed an initial increase immediately post dosing followed by a severe decrease (−163% to −435%). Maximal effects were observed at approximately 10-15 minutes into the infusion and returned gradually toward baseline at the end of the 60 minutes monitoring period, with the exception of MAP of one animal out of two where the decrease was sustained. Increased contractility and decreased LVEDP were noted throughout the monitoring period. Similar hemodynamic changes were observed with the initiation of the second infusion (30 mg/kg) with the exception of HR and contractility, which presented a second increase (+158 to +174% and +25% to +33% respectively). These cardiovascular changes correlate with plasma histamine levels. The severity of tachycardia increased above 200% of baseline after completion of dosing at 30 mg/kg. At 90 mg/kg, as for the Group 1 animals, all animals succumbed at the completion of the final 15-minute infusion as progressive and severe hypotension was noted.

While the invention has been described in conjunction with the above embodiments, that the foregoing description and examples are intended to illustrate and not to limit the scope of the invention. Other aspects, advantages and modifications within the scope of the invention will be apparent to those skilled in the art to which the invention pertains.

The invention claimed is:

1. A method of administering to a subject a composition comprised of an active agent that is 4-methoxy-N-(3,5-bis-(1-pyrrolidinyl)-4-hydroxy benzyl)benzene sulfonamide or a pharmaceutically acceptable salt thereof, the method comprising intravenously administering said composition substantially evenly to said subject over a period that is greater than about 15 minutes.

2. The method according to claim 1, wherein said period is from about 30 minutes to about 120 minutes.

3. The method according to claim 1, wherein said period is from about 30 minutes to about 60 minutes.

4. A method of administering to a subject a composition comprised of an active agent that is 4-methoxy-N-(3,5-bis-(1-pyrrolidinyl)-4-hydroxy benzyl)benzene sulfonamide or a pharmaceutically acceptable salt thereof, the method comprising intravenously administering said composition to said subject over a period of greater than about 15 minutes, wherein no more than about 1 mg/kg of said active agent is administered to said subject per minute.

5. The method according to claim 4, wherein no more than about 0.5 mg/kg of said active agent is administered to said subject per minute.

6. The method according to claim 4, wherein no more than about 0.1 mg/kg of said active agent is administered to said subject per minute.

7. A method according to claim 1, wherein said active agent is 4-methoxy-N-(3,5-bis-(1-pyrrolidinyl)-4-hydroxy benzyl) benzene sulfonamide sulfate.

8. A method according to claim 1, wherein said subject suffers or is at risk of suffering from a cardiac arrhythmia.

9. A method according to claim 8, wherein said cardiac arrhythmia is selected from the group consisting of supraventricular tachyarrhythmia, premature ventricular contractions, ventricular tachycardia, and ventricular fibrillation, atrial fibrillation, and combinations thereof.

10. The method according to claim 1, wherein said composition further comprises a pharmaceutically acceptable excipient.

11. A method according to claim 10, wherein said pharmaceutically acceptable excipient is selected from the group consisting of a buffer, a diluent, a stabilizer, and combinations thereof.

12. The method according to claim 4, wherein said composition further comprises a pharmaceutically acceptable excipient.

13. A method according to claim 12, wherein said pharmaceutically acceptable excipient is selected from the group consisting of a buffer, a diluent, a stabilizer, and combinations thereof.

14. A method according to claim 2, wherein said active agent is 4-methoxy-N-(3,5-bis-(1-pyrrolidinyl)-4-hydroxy benzyl)benzene sulfonamide sulfate.

15. A method according to claim 3, wherein said active agent is 4-methoxy-N-(3,5-bis-(1-pyrrolidinyl)-4-hydroxy benzyl)benzene sulfonamide sulfate.

16. A method according to claim 4, wherein said active agent is 4-methoxy-N-(3,5-bis-(1-pyrrolidinyl)-4-hydroxy benzyl)benzene sulfonamide sulfate.

17. A method according to claim 5, wherein said active agent is 4-methoxy-N-(3,5-bis-(1-pyrrolidinyl)-4-hydroxy benzyl)benzene sulfonamide sulfate.

18. A method according to claim 6, wherein said active agent is 4-methoxy-N-(3,5-bis-(1-pyrrolidinyl)-4-hydroxy benzyl)benzene sulfonamide sulfate.

* * * * *